(12) United States Patent
Matsukura et al.

(10) Patent No.: US 7,442,815 B2
(45) Date of Patent: Oct. 28, 2008

(54) ULTRAVIOLET TRANSMITTING FLUOROPOLYMER AND PELLICLE COMPRISING SAID POLYMER

(75) Inventors: Ikuo Matsukura, Kanagawa (JP); Hidekazu Okamoto, Kanagawa (JP); Eisuke Murotani, Kanagawa (JP); Kazuya Oharu, Kanagawa (JP)

(73) Assignee: Asahi Glass Company, Limited, Tokyo (JP)

( * ) Notice: Subject to any disclaimer, the term of this patent is extended or adjusted under 35 U.S.C. 154(b) by 628 days.

(21) Appl. No.: 11/061,689

(22) Filed: Feb. 22, 2005

(65) Prior Publication Data

US 2005/0147897 A1 Jul. 7, 2005

Related U.S. Application Data

(63) Continuation of application No. PCT/JP03/10588, filed on Aug. 21, 2003.

(30) Foreign Application Priority Data

Aug. 21, 2002 (JP) ............................. 2002-240759

(51) Int. Cl.
*C07D 307/77* (2006.01)
(52) U.S. Cl. ...................................... 549/504
(58) Field of Classification Search .................. 549/504
See application file for complete search history.

(56) References Cited

U.S. PATENT DOCUMENTS

| 3,865,845 | A | 2/1975 | Resnick |
| 6,548,129 | B2 | 4/2003 | Matsukura et al. |
| 6,660,346 | B2 | 12/2003 | Matsukura et al. |
| 2004/0048005 | A1 | 3/2004 | Matsukura et al. |
| 2004/0071899 | A1 | 4/2004 | Matsukura et al. |
| 2005/0147897 | A1 | 7/2005 | Matsukura et al. |

FOREIGN PATENT DOCUMENTS

| JP | 3-39963 | 2/1991 |
| JP | 3-67262 | 3/1991 |
| JP | 10-31119 | 2/1998 |
| JP | 2001-330943 | 11/2001 |
| WO | WO 01/37044 | 5/2001 |
| WO | WO 02/066452 | 8/2002 |
| WO | WO 02/092670 | 11/2002 |

OTHER PUBLICATIONS

U.S. Appl. No. 11/061,689, filed Feb. 22, 2005, Matsukura, et al.
U.S. Appl. No. 11/446,242, filed Jun. 5, 2006, Matsukura, et al.

*Primary Examiner*—Taofiq A Solola
(74) *Attorney, Agent, or Firm*—Oblon, Spivak, McClelland, Maier & Neustadt, P.C.

(57) ABSTRACT

A pellicle which is excellent in transmittance and durability against short wavelength light, and which can be used for photolithography by using e.g. a KrF excimer laser, is provided.

A pellicle for exposure to a light having a wavelength of at most 200 nm, which comprises a frame and a pellicle membrane bonded to the frame by means of an adhesive, wherein the pellicle membrane and/or the adhesive comprises a polymer containing repeating units represented by the following formula (1):

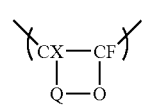

(1)

wherein Q represents a $C_{1-3}$ polyfluoroalkylene group having a linear structure, or a group having at least one atom selected from hydrogen atoms and fluorine atoms in such a polyfluoroalkylene group substituted by a substituent comprising a polyfluoroalkyl group which may contain an ethereal oxygen atom, or the like, and X represents a hydrogen atom, a fluorine atom or a $C_{1-3}$ polyfluoroalkyl group which may contain an ethereal oxygen atom.

7 Claims, No Drawings

ULTRAVIOLET TRANSMITTING FLUOROPOLYMER AND PELLICLE COMPRISING SAID POLYMER

TECHNICAL FIELD

The present invention relates to a novel fluoromonomer, and a pellicle membrane and an adhesive for a pellicle membrane, comprising a fluoropolymer containing the fluoromonomer as the main component and having high transparency in the ultraviolet light region. Further, it relates to an exposure method employing said pellicle.

BACKGROUND ART

A fluoropolymer having a saturated cyclic structure in its main chain is amorphous and has been known to be a transparent fluoropolymer. Such a transparent fluoropolymer has been used as a transparent coating material, optical material, etc. (JP-A-3-39963 and JP-A-3-67262). Further, a substantially linear fluoropolymer containing hydrogen in its main chain (JP-A-2001-330943) and a polymer containing perfluoro-1,3-dioxol or the like (WO2001/37044) has been known to be highly transparent in the ultraviolet region. Such materials have been applied to e.g. a pellicle material.

A pellicle is, in photolithography as one process in production of a semiconductor device or a liquid crystal display panel, a protective film to be mounted on a pattern of a mask to prevent foreign substances from getting on a photo mask or a reticle (hereinafter they will generically be referred to as mask), thereby to prevent pattern defect at the time of exposure. Usually, a pellicle has such a structure that a transparent thin membrane attached to a frame by means of an adhesive, is disposed on a mask with a certain distance from the mask surface.

In the filed of production of a semiconductor device and a liquid crystal display panel, in which such a pellicle is used, as the wiring and the wiring distance become fine progressively, the wavelength of a light source to be used becomes short rapidly in photolithography also. In recent years, a KrF excimer laser has been introduced for wiring processing with a minimum pattern dimension of at most 0.3 μm. The oscillation wavelength thereof is 248 nm, and a conventional nitrocellulose type membrane material is insufficient in durability. Thus, an amorphous perfluoropolymer as disclosed in e.g. JP-A-3-39963 has been found to be useful as a membrane material.

DISCLOSURE OF THE INVENTION

On the other hand, in lithography in recent years, wiring processing with a minimum pattern dimension of at most 0.2 μm is required. For such processing, as a laser at a wavelength of at most 200 nm, use of e.g. an argon fluoride excimer laser at a wavelength of 193 nm (hereinafter referred to as ArF excimer laser) or a fluorine gas excimer laser at a wavelength of 157 nm (hereinafter referred to as $F_2$ excimer laser) has been studied.

However, a laser light from such a laser has an extremely high energy, and thus even the amorphous perfluoropolymer as disclosed in JP-A-3-39963 is insufficient in durability. For example, a perfluoropolymer disclosed in the document (CYTOP, trade name, manufactured by ASAHI GLASS COMPANY, LIMITED) has such properties that its light transmittance and durability rapidly decrease against a light of at most 170 nm. Accordingly, the transmittance of the perfluoropolymer against a $F_2$ excimer laser light at a wavelength of 157 nm is remarkably low. Further, it is excellent in transparency against a light of at least 170 nm, however, its membrane strength is not necessarily sufficient, and its handling tends to be difficult.

Further, as a pellicle membrane with which a $F_2$ excimer laser light can be used, JP-A-2001-330943 discloses a linear fluoropolymer, and WO2001/37044 discloses a copolymer containing e.g. vinylidene fluoride as the main component. However, these fluoropolymers have transparency at 157 nm, they are insufficient in durability.

Further, an adhesive which bonds a pellicle membrane to a frame also has similar problems of deterioration by stray light or reflected light of a laser light, and accordingly development of an adhesive having high durability has been desired.

The present inventors have found that a polymer containing specific repeating units has high transmittance and durability against a laser light at a wavelength of at most 200 nm, preferably at most 180 nm (hereinafter such laser lights will generically be referred to as short wavelength light), and that it is excellent in transparency and durability in the short wavelength light region. Further, they have found that an optimum pellicle as a pellicle for an ArF excimer laser light or a pellicle for exposure to a light having a wavelength of at most 180 nm, which is shorter than the ArF excimer laser light, specifically, a pellicle for exposure to a $F_2$ excimer laser light having a wavelength of 157 nm, by using the polymer as a pellicle membrane and/or an adhesive for a pellicle membrane.

Namely, the present invention provides the followings.

<1> A pellicle for exposure to a light having a wavelength of at most 200 nm, which comprises a frame and a pellicle membrane bonded to the frame by means of an adhesive, characterized in that the pellicle membrane and/or the adhesive comprises a polymer containing repeating units represented by the following formula (1):

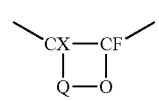

wherein Q represents a $C_{1-3}$ polyfluoroalkylene group having a linear structure, or a group having at least one atom selected from hydrogen atoms and fluorine atoms in such a polyfluoroalkylene group substituted by a monovalent substituent comprising a polyfluoroalkyl group which may contain an ethereal oxygen atom, provided that when two or more such monovalent substituents are present, two of such monovalent substituents together may form a bivalent substituent comprising a polyfluoroalkylene group which may contain an ethereal oxygen atom, and X represents a hydrogen atom, a fluorine atom or a $C_{1-3}$ polyfluoroalkyl group which may contain an ethereal oxygen atom.

<2> The pellicle according to <1>, wherein Q is a $C_{1-3}$ perfluoroalkylene group having a linear structure, or a group having at least one of fluorine atoms in such a perfluoroalkylene group substituted by a monovalent substituent comprising a perfluoroalkyl group which may contain an ethereal oxygen atom, and X is a hydrogen atom, a fluorine atom or a $C_{1-3}$ polyfluoroalkyl group which may contain an ethereal oxygen atom.

<3> The pellicle according to <1>, wherein the repeating units represented by the formula (1) are repeating units represented by the following formula (2):

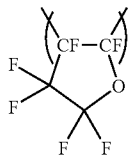

(2)

<4> The pellicle according to <1>, <2> or <3>, wherein the pellicle membrane comprises a polymer having repeating units represented by the formula (1) as an essential component, and having no functional group.

<5> The pellicle according to any one of <1> to <4>, wherein the adhesive comprises a polymer having repeating units represented by the formula (1) as an essential component, and having functional groups.

<6> The pellicle according to any one of <1> to <5>, wherein the polymer containing repeating units represented by the formula (1) is a polymer having no —CH$_2$CH$_2$— structure.

<7> An exposure method employing a light having a wavelength of at most 200 nm in photolithography, characterized in that the pellicle as defined in any one of <1> to <6> is used.

<8> 2,2,3,3,4,5-hexafluoro-2,3-dihydrofuran.

<9> A polymer having polymer units represented by the following formula (2) as an essential component:

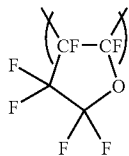

(2)

<10> A polymer comprising polymer units represented by the following formula (2) and having a molecular weight of from 500 to 1,000,000, or a polymer comprising polymer units represented by the formula (2) and one or more types of polymer units of other polymerizable monomers, and having a molecular weight of from 500 to 1,000,000, characterized in that when polymer units of other polymerizable monomers are contained, the proportion of the polymer units represented by the formula (2) in the polymer is at least 0.01 mass % and less than 100 mass %:

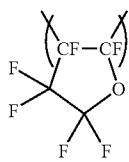

(2)

<11> A method for producing a polymer having polymer units represented by the following formula (2) as an essential component, which comprises homopolymerizing 2,2,3,3,4,5-hexafluoro-2,3-dihydrofuran, or copolymerizing 2,2,3,3,4,5-hexafluoro-2,3-dihydrofuran with one or more types of other polymerizable monomers:

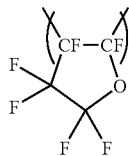

(2)

BEST MODE FOR CARRYING OUT THE INVENTION

According to the present invention, a specific polymer containing fluorine atoms is used as a pellicle membrane and/or an adhesive for a pellicle membrane in a pellicle. Further, a pellicle to be used for short wavelength photolithography is provided. The pellicle membrane employing the specific polymer of the present invention has favorable transparency and excellent durability against light. Further, the adhesive of the present invention employing the specific polymer has excellent adhesive properties and durability. Thus, by using the pellicle of the present invention for a process of photolithography in production of a semiconductor device, a semiconductor device can be produced with high yield.

Further, according to the present invention, 2,2,3,3,4,5-hexafluoro-2,3-dihydrofuran which is a novel compound to be useful for e.g. production of a pellicle, and a novel copolymer obtained from 2,2,3,3,4,5-hexafluoro-2,3-dihydrofuran, are provided.

The polymer of the present invention is a polymer having repeating units of the cyclic structure represented by the formula (1) (hereinafter sometimes referred to as polymer (1)). In the present specification, a group having hydrogen atoms and having one or more hydrogen atoms fluorinated, is represented as a polyfluoro group, and a group having all the hydrogen atoms substituted by fluorine atoms is represented as a perfluoro group.

As Q in the formula (1), the C$_{1-3}$ polyfluoroalkylene group having a linear structure is a group represented by —(CH$_2$)$_k$— (k represents an integer of from 1 to 3) and having one or more hydrogen atoms substituted by fluorine atoms.

In a case where Q is a group having at least one atom selected from hydrogen atoms and fluorine atoms in a polyfluoroalkylene group substituted by a monovalent substituent comprising a polyfluoroalkyl group which may contain an ethereal oxygen atom, the carbon number of such a monovalent substituent is preferably from 1 to 3.

Further, in a case where two or more such monovalent substituents are present, two of such monovalent substituents together may form a bivalent substituent comprising a polyfluoroalkylene group which may contain an ethereal oxygen atom. For example, when three or more monovalent substituents are present, two of such monovalent substituents together form a polyfluoroalkylene group which may contain an ethereal oxygen atom, and the other monovalent substituents may be polyfluoroalkyl groups which may contain an ethereal oxygen atom.

The carbon number of such a monovalent substituent is preferably from 1 to 3. The carbon number of such a bivalent substituent is preferably from 3 to 5. Further, when the substituent is a group containing an ethereal oxygen atom, the number of the ethereal oxygen atom is preferably one, and the monovalent substituent is preferably a polyfluoroalkoxy group, and the bivalent substituent is preferably a perfluoro(alkyleneoxyalkylene) group.

The group as a substituent is preferably a highly fluorinated group, preferably a group having a proportion of the number of fluorine atoms to the total number of fluorine atoms and hydrogen atoms bonded to carbon atoms of at least 80%, and preferably a perfluorinated group having the proportion of 100%, in view of the stability of the polymer (1). For example, the monovalent substituent is preferably a perfluoroalkyl group which may contain an ethereal oxygen atom, particularly preferably a trifluoromethyl group. The bivalent substituent is preferably a perfluoroalkylene group which may contain an ethereal oxygen atom, particularly preferably a perfluoroalkylene group, especially preferably a perfluorodimethylene group or a perfluorotrimethylene group.

Such a substituent is a group to be a side chain of the cyclic structure. The number of the monovalent substituent is not particularly limited, preferably from 1 to 4, more preferably 1 or 2. The number of the bivalent substituent is 1.

Q is preferably a $C_{1-3}$ perfluoroalkylene group having a linear structure, or a group having at least one fluorine atom in such a perfluoroalkylene group substituted by a monovalent substituent comprising a perfluoroalkyl group which may contain an ethereal oxygen atom, and such a monovalent substituent is preferably the above group.

Further, the monovalent substituent is bonded to the carbon atom at the terminal of Q, particularly, it is more preferably bonded to the carbon atom adjacent to the ethereal oxygen atom to which Q is bonded. In such a case, a fast polymer (1) having mechanical strength is obtained. The reason is considered that the polymer has high mechanical strength since the side chain is bonded to the carbon atom adjacent to the ethereal oxygen atom, and on the other hand, the side chain imparts some flexibility to the polymer, which prevents the polymer from being too hard and fragile.

As specific examples of Q, the following examples may be mentioned. Q is represented in the direction of —CX-Q-O—:
—(CF$_2$)$_2$—, —CF$_2$CF(OCF$_3$)—, —(CF(CF$_3$)CF$_2$—, —CF$_2$CF(CF$_3$)—, —CF(OCF$_3$)CF(OCF$_3$)—, —CF$_2$C(CF$_3$)$_2$—, —CF(CF$_3$)CF(CF$_3$)—, —CF(OCF$_3$)C(OCF$_3$)(CF$_3$)—, —C(OCF$_3$)(CF$_3$)CF(OCF$_3$)—, —C(OCF$_3$)$_2$CF(CF$_3$)—,

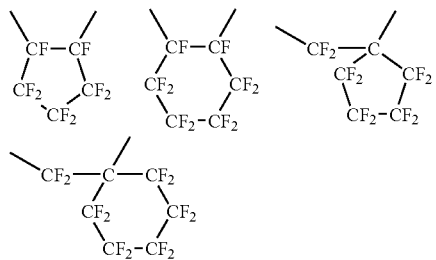

In the formula (1), X represents a hydrogen atom, a fluorine atom or a $C_{1-3}$ polyfluoroalkyl group which may contain an ethereal oxygen atom, and it is preferably a hydrogen atom, a fluorine atom or a $C_{1-3}$ perfluoroalkyl group which may contain an ethereal oxygen atom. X is preferably a hydrogen atom or a fluorine atom, since the polymerizability in the polymerization reaction as described hereinafter will be high, and it is preferably a fluorine atom in view of durability of a pellicle against light.

As the repeating units represented by the formula (1), preferred is a case where X is a fluorine atom and Q is a group having no substituent, particularly preferred is a case where Q is —(CF$_2$)$_k$— (wherein k is an integer of from 1 to 3, preferably 2 or 3), and especially preferred are repeating units represented by the following formula (2) wherein k is 2:

The polymer of the present invention may be a polymer comprising repeating units represented by the formula (1) alone, or a polymer comprising repeating units represented by the formula (1) and one or more types of repeating units other than the above repeating units (hereinafter referred to as other repeating units). Further, the molecular weight of the polymer is preferably from 500 to $1 \times 10^6$, particularly preferably from 500 to $2 \times 10^5$, especially preferably from 500 to $1 \times 10^5$.

The polymer is preferably obtained, in a usual case, by a method of polymerizing a polymerizable monomer represented by the following formula (1M) (hereinafter referred to as monomer (1M)) alone to obtain a polymer comprising repeating units represented by the formula (1) alone, a method of copolymerizing the monomer (1M) and a polymerizable monomer which is polymerizable with the monomer (1M) (hereinafter referred to as the other monomer (3M)), or a method of carrying out chemical conversion after polymerization as described hereinafter:

wherein X and Q are as defined above, and the preferred modes thereof are also as defined above.

The monomer (1M) is preferably a monomer represented by the following formula (2M) (hereinafter referred to as monomer (2M)). The repeating units obtained by polymerizing the monomer (2M) are repeating units represented by the above formula (2):

The monomer (1M) may be prepared in accordance with a known method by the present applicant (WO00/56694, WO02/4397). A typical example of a preferred process for producing the monomer (2M) is represented by the following formula.

Namely, the monomer (2M) (2,2,3,3,4,5-hexafluoro-2,3-dihydrofuran) may be produced in such a manner that tetrahydrofurfuryl alcohol which is industrially available at a low cost is reacted with a compound having a fluorinated group (Q$^1$) and a —COX$^1$ (wherein X$^1$ represents a fluorine atom or a chorine atom) to form a partially fluorinated ester, the C—H structure in the partially fluorinated ester is fluorinated by a fluorination reaction such as liquid phase fluorination and converted into C—F, and the ester is pyrolyzed, or the ester linkage in the ester is decomposed, followed by pyrolysis. A typical example of the production process may be represented by the following formula. $X^1$ in the formula represents a fluorine atom or a chlorine atom as defined above, $Q^1$ represents a n-valent fluorinated organic group, $Q^{1f}$ represents a perfluorinated n-valent organic group, and n represents the number of the group bonded to $Q^1$ or $Q^{1f}$ and is an integer of at least 1:

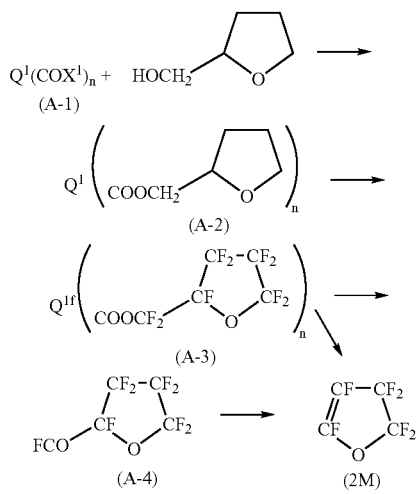

Namely, a process of reacting a compound (A-1) with 2-tetrahydrofurfuryl alcohol to obtain a compound (A-2), perfluorinating the compound (A-2) to obtain a compound (A-3), and pyrolyzing the compound (A-3) to obtain a compound represented by the formula (2M), or decomposing the ester linkage of the compound (A-3) to obtain a compound (A-4) and then pyrolyzing the compound (A-4) to obtain a monomer (2M), may be mentioned as an example. The above reactions may be carried out in accordance with conditions for the respective reaction steps and operation methods at the time of reactions as disclosed in e.g. WO00/56694 and WO02/4397. $Q^1$ is preferably the same group as $Q^{1f}$, $X^1$ is preferably a fluorine atom, and n is preferably an integer of from 1 to 4 (particularly preferably 1 or 2).

The compound (2M) obtained by the above production process (i.e. 2,2,3,3,4,5-hexafluoro-2,3-dihydrofuran) is a novel compound. The compound may be used for various applications by polymerizing it as a polymerizable monomer. For example, it may be useful in production of a pellicle. Further, it is useful as e.g. a low reflection processing material, a chemical resistant coating material, a water and oil repellant material, a material for a core and a clad of an optical fiber, an optical waveguide material, an electronic component material and a film material.

When the polymer of the present invention is obtained by copolymerizing the monomer (1M) and the other monomer (3M), the type of the other monomer (3M) and its proportion copolymerized are optional. Further, when the polymer contains two or more monomer units, the monomer units are aligned in the form of a block or a graft or randomly. However, if they are aligned in the form of a block or a graft, the chain of the same monomer tends to be long and there is a possibility that durability against light is decreased, and accordingly they are aligned preferably randomly.

The proportion of the repeating units (1) based on the monomer (1M) in the polymer is preferably from 1 to 100 mol %, particularly preferably from 5 to 80 mol %, especially preferably from 10 to 70 mol %, based on the entire repeating units. However, when the polymer containing repeating units represented by the formula (1) is used for an adhesive as described hereinafter, the proportion of the repeating units may be small, and it may be at most 1 mol %.

The other monomer (3M) may be a monomer containing fluorine atoms or a monomer containing no fluorine atom, and a fluorinated monomer, a hydrocarbon type monomer or another monomer may be used. The other monomer (3M) is preferably a monomer forming no —$CH_2CH_2$— chain structure when formed into a polymer, and preferably one or more types of monomers selected from the following monomers (3M-1), (3M-2) and (3M-3).

The monomer (3M-1) is a monomer represented by $CHR^1=CR^2R^3$ (wherein each of $R^1$, $R^2$ and $R^3$ which are independent of one another, represents a hydrogen atom, a halogen atom or a monovalent fluorinated saturated organic group, and $R^1$, $R^2$ and $R^3$ are not hydrogen atoms at the same time), preferably a $C_{2-3}$ fluorinated olefin.

As specific examples of the monomer (3M-1), halogenoolefins such as vinyl fluoride, 1,2-difluoroethylene, vinylidene fluoride, trifluoroethylene and vinylidene fluoride may be mentioned. Among them, as the monomer (3M-1), vinylidene fluoride, vinyl fluoride or trifluoroethylene is particularly preferred.

The monomer (3M-2) is a monomer represented by $CFR^4=CR^5R^6$ (wherein each of $R^4$, $R^5$ and $R^6$ which are independent of one another, represents a fluorine atom or a monovalent fluorinated saturated organic group, or two groups selected from $R^4$, $R^5$ and $R^6$ together form a bivalent fluorinated organic group, and the other one group is a fluorine atom or a monovalent fluorinated saturated organic group).

The monomer (3M-2) is preferably a monomer wherein $R^4$, $R^5$ and $R^6$ are as defined by the latter (i.e. two groups selected from $R^4$, $R^5$ and $R^6$ together form a bivalent fluorinated organic group (preferably a bivalent fluorinated saturated organic group), and the other one group represents a fluorine atom or a monovalent fluorinated saturated organic group) (hereinafter referred to as monomer (3M-20)).

The monomer (3M-20) is a monomer having a fluorine atom and having a cyclic structure. The monomer (3M-20) may, for example, be a monomer represented by the following formula (3M-21), a monomer represented by the following formula (3M-22) or a monomer represented by the following formula (3M-23):

(3M-21)

(3M-22)

(3M-23)

wherein each of $R^{11}$ to $R^{17}$ which are independent of one another, represents a fluorine atom or a monovalent fluorinated saturated organic group. $R^{11}$ and $R^{12}$ together may form a bivalent fluorinated organic group. When each of $R^{11}$ to $R^{17}$ is a monovalent fluorinated saturated organic group, it is preferably a perfluoroalkyl group or a perfluoroalkoxy group, particularly preferably such a group having a carbon number of 1 or 2.

The monomer (3M-20) is preferably a monomer wherein $R^{11}$ and $R^{12}$ are trifluoromethyl groups (i.e. perfluoro(2,2-dimethyl-1,3-dioxole)), a monomer represented by the following formula (3M-24) wherein $R^{11}$ and $R^{12}$ together form a bivalent fluorinated organic group, or a monomer wherein $R^{15}$ and $R^{16}$ are trifluoromethyl groups (i.e. perfluoro(2-methylene-4-methyl-1,3-dioxolane)):

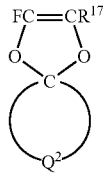

(3M-24)

In the formula (3M-24), $R^{17}$ represents a fluorine atom or a hydrogen atom, and $Q^2$ represents a linear fluorinated alkylene group containing two or more hetero atoms (preferably ethereal oxygen atoms) or such a group substituted by a fluorinated alkyl group.

The monomer (3M-2) other than the monomer (3M-20) may, for example, be a perfluoroolefin such as tetrafluoroethylene or hexafluoropropylene; or a perfluoro(alkyl vinyl ether) such as perfluoro(methyl vinyl ether) or perfluoro(propyl vinyl ether).

The monomer (3M-3) is a monomer represented by the formula $CR^7R^8=CR^9-Q^3-CR^1=CF_2$ (wherein each of $R^7$, $R^8$, $R^9$ and $R^{10}$ which are independent of one anther, represents a hydrogen atom, a fluorine atom or a monovalent fluorinated organic group, and $Q^3$ represents a bivalent fluorinated organic group).

Each of $R^7$, $R^8$ and $R^9$ which are independent of one another, is preferably a hydrogen atom or a fluorine atom, and particularly when at least one of $R^7$ and $R^8$ is a fluorine atom, $R^9$ is preferably a hydrogen atom, and when $R^7$ and $R^8$ are hydrogen atoms at the same time, $R^9$ is preferably a hydrogen atom or a fluorine atom. $R^{10}$ is preferably a fluorine atom, a trifluoromethyl group or a pentafluoroethyl group, particularly preferably a fluorine atom.

$Q^3$ is preferably a $C_{1-10}$ perfluoroalkylene group which may contain an ethereal oxygen atom, and preferably such a group having a linear structure or a branched structure.

In a case where $Q^3$ is a $C_{1-10}$ perfluoroalkylene group containing no ethereal oxygen atom, the carbon number is preferably from 2 to 6.

In a case where $Q^3$ is a perfluoroalkylene group having an ethereal oxygen atom, the number of the ethereal oxygen atom may be one or more. The ethereal oxygen atom may be bonded to one or both of the terminals of the perfluoroalkylene group, or may be inserted between the carbon-carbon linkage.

When $Q^3$ is a perfluoroalkylene group having an ethereal oxygen atom, the length (here, the length means the minimum number of atoms from $CR^9$ to $CR^{10}$) of $Q^3$ is preferably 2 to 4 atoms, particularly preferably 2 to 3 atoms. The length is preferably two atoms consisting of one carbon atom and one oxygen atom, three atoms consisting of two carbon atoms and one oxygen atom, or three atoms consisting of one carbon atom and two oxygen atoms.

Further, $Q^3$ is preferably a group selected from a $C_{1-3}$ perfluoroalkylene group having an ethereal oxygen atom at the terminal which is bonded to the carbon atom to which $R^{10}$ is bonded, a $C_{1-2}$ perfluoroalkylene group having ethereal oxygen atoms on both terminals, and a $C_{1-4}$ perfluoroalkylene group having no ethereal oxygen atom, or such a selected group having at least one fluorine atom substituted by a $C_{1-3}$ perfluoroalkyl group (preferably trifluoromethyl group).

Further, $Q^3$ is particularly preferably a $C_{1-2}$ perfluoroalkylene group having an ethereal oxygen atom at the terminal which is bonded to the carbon atom to which $R^{10}$ is bonded, or such a group having at least one fluorine atom substituted by a $C_{1-3}$ perfluoroalkyl group (preferably trifluoromethyl group).

The monomer (3M-3) may be a monomer represented by $CH_2=CH-Q^{3f}-O-CF=CF_2$ or a monomer represented by $CF_2=CH-Q^{3f}-O-CF=CF_2$ (wherein $Q^{3f}$ represents a $C_{1-3}$ perfluoroalkylene group, preferably such a group having a carbon number of from 1 to 2). $Q^{3f}$ is preferably a $C_{1-3}$ linear perfluoroalkylene group or a branched perfluoroalkylene group having from 1 to 3 fluorine atoms in such a linear perfluoroalkylene group substituted by a $C_{3-1}$ perfluoroalkyl group, and as the latter group, preferred is a group having from 1 to 2 fluorine atoms substituted by a trifluoromethyl group.

As specific examples of the monomer (3M-3), the following compounds may be mentioned.

$CH_2=CHCF_2CF_2OCF=CF_2$,
$CH_2=CHCF_2CF_2CF_2OCF=CF_2$,
$CH_2=CHCF_2OCF=CF_2$,
$CH_2=CHCF(CF_3)CF_2OCF=CF_2$,
$CF_2=CHCF(CF_3)CF_2OCF=CF_2$,
$CH_2=CHOC(CF_3)_2OCF=CF_2$,
$CH_2=CFCF_2CF_2OCF=CF_2$,
$CH_2=CFCF(CF_3)CF_2OCF=CF_2$,
$CF_2=CHCF_2CF_2OCF=CF_2$,
$CF_2=CHCF(CF_3)CF_2OCF=CF_2$,
$CFH=CHCF_2CF_2OCF=CF_2$,
$CFH=CHCF(CF_3)CF_2OCF=CF_2$.

Among them, the following monomers are particularly preferred as the monomer (3M-3):

$CH_2=CFCF_2CF_2OCF=CF_2$,
$CH_2=CFCF(CF_3)CF_2OCF=CF_2$,
$CF_2=CHCF_2CF_2OCF=CF_2$,
$CF_2=CHCF(CF_3)CF_2OCF=CF_2$,
$CFH=CHCF_2CF_2OCF=CF_2$,
$CFH=CHCF(CF_3)CF_2OCF=CF_2$.

Further, as the monomer (3M-3), $CF_2=CHCF(CF_3)CF_2OCF=CF_2$ is especially preferred.

The structure of repeating units obtained by polymerizing the monomer (3M-3) may be represented by the following formula (3M-30), (3M-31) or (3M-32):

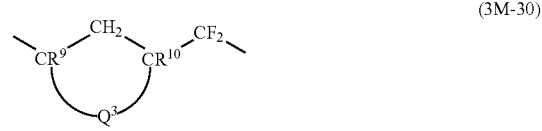

(3M-30)

-continued

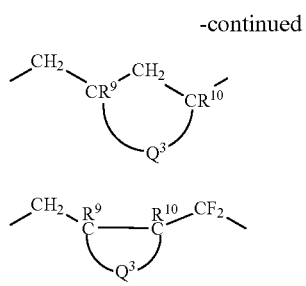
(3M-31)

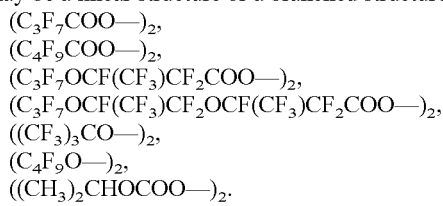
(3M-32)

The polymer (1) of the present invention is preferably a copolymer of the monomer (1M) and the monomer (3M-1) or a copolymer of the monomer (1M) and the monomer (3M-3).

When the polymer (1) of the present invention is obtained by a polymerization reaction, the method is not particularly limited, and a method such as bulk polymerization, suspension polymerization or solution polymerization may be employed. The polymerization reaction is carried out preferably in a solvent such as water or an organic solvent, with a view to suppressing decomposition of the monomer due to abnormal polymerization or sudden heat generation. As the solvent, a known polymerization solvent may be used, however, it is selected preferably from organic solvents containing no chlorine atom, so as to improve durability of the obtained polymer against light.

Further, when the polymerization reaction is carried out employing a polymerization initiator, when formation of a —CH— chain as a chain derived from the polymerization initiator on e.g. the terminal of the polymer should be avoided, it is preferred to use, as the polymerization initiator, a polymerization inhibitor comprising a perfluorinated compound, and it is preferred to use e.g. a polymerization initiator comprising a compound having a small carbon number (preferably a carbon number of from 1 to 3) at the perfluoroalkyl group moiety, or a polymerization initiator comprising a compound having a polyether moiety.

As the polymerization initiator, the following compounds may be mentioned. In the following formulae, the structure of a perfluoroalkyl group having a carbon number of at least 3 may be a linear structure or a branched structure.

$(C_3F_7COO—)_2$,
$(C_4F_9COO—)_2$,
$(C_3F_7OCF(CF_3)CF_2COO—)_2$,
$(C_3F_7OCF(CF_3)CF_2OCF(CF_3)CF_2COO—)_2$,
$((CF_3)_3CO—)_2$,
$(C_4F_9O—)_2$,
$((CH_3)_2CHOCOO—)_2$.

The temperature at the polymerization reaction is preferably from −10° C. to +150° C., particularly preferably from 0° C. to 120° C. If the polymerization temperature is too high, a polymer containing a large amount of a chain structure formed by polymerization of another monomer in the same molecule may form. If the polymerization temperature is too low, the yield of the polymer (1) may extremely decrease. Further, the pressure at the polymerization reaction may be any pressure of reduced pressure, atmospheric pressure and elevated pressure. It is usually preferably a level of from the atmospheric pressure to 2 MPa (gauge pressure, hereinafter the pressure will be represented by the gauge pressure unless otherwise specified), particularly preferably from the atmospheric pressure to 1 MPa.

The polymer (1) formed by the polymerization reaction may be subjected to e.g. a treatment with fluorine as the case requires to convert the terminal groups. By such a treatment, unfavorable terminal groups which may form during the polymerization or an unsaturated moiety may be converted e.g. by addition of fluorine, and the polymer may be converted into a polymer which is more excellent in durability. For example, a treatment method of bringing a fluorine gas into contact with the polymer at a temperature of at most 250° C., preferably a treatment method of bringing a fluorine gas into contact with the polymer at a temperature of at most 200° C., may be mentioned. The treatment with fluorine may be carried out by bringing the polymer in a solid state into contact with the fluorine gas or bringing the polymer in a solution state into contact with the fluorine gas. By such a treatment, terminal groups such as —CH=CH$_2$ which may form at the terminals of the polymer may be converted into groups such as —CF$_3$ and —CF$_2$H.

The polymer (1) of the present invention is a polymer having repeating units represented by the formula (1) as an essential component, i.e. a polymer having a saturated cyclic structure as an essential component in the main chain of the polymer. The saturated cyclic structure makes the polymer (1) of the present invention be an amorphous and highly transparent polymer. Further, the cyclic structure has an effect to split a long electronic conjugation in the polymer chain, and accordingly the polymer (1) of the present invention is a polymer which is transparent also in the short wavelength region at a wavelength of at most 200 nm.

Further, the polymer (1) of the present invention has such properties that it has high durability against light in the short wavelength region. The reason why the polymer has such properties is not necessarily clear, but is considered to be because the strain of the saturated cyclic structure in the main chain is small, and thus the polymer is less likely to undergo cleavage of the main chain even if it absorbs light.

In the present invention, in a pellicle for exposure to a light having a wavelength of at most 200 nm, which comprises a frame and a pellicle membrane bonded to the frame by means of an adhesive, the polymer (1) is used for the pellicle membrane and/or the adhesive. Namely, according to the present invention, an exposure method employing a light having a wavelength of at most 200 nm in lithography may be carried out by employing the pellicle of the present invention. The pellicle of the present invention is to prevent the decrease in yield by attachment of dusts on a mask and a reticle used in exposure to a light having a wavelength of at most 200 nm, particularly an excimer laser light. The pellicle of the present invention can be applied to any exposure, but is preferably used in exposure in photolithography which is one process in production of a semiconductor device or a liquid crystal display panel. Particularly, it has high level durability against a KrF excimer laser light (wavelength 248 nm) and ArF excimer laser light (wavelength 193 nm).

The pellicle of the present invention comprises a pellicle membrane and a frame, and the pellicle membrane is bonded to the frame by means of an adhesive. The material forming the frame is not particularly limited so long as it can support the pellicle membrane. A metal material is preferred in view of strength, and a metal material having durability against a short wavelength light of at most 200 nm to be used for exposure, may be employed without any restriction. The material forming the frame may, for example, be aluminum, 18-8 stainless steel, nickel, synthetic quartz, calcium fluoride or barium fluoride. Among them, aluminum or synthetic quartz is preferred as the material in view of environmental resistance, strength and specific gravity.

In the present invention, the polymer (1) is used as the pellicle membrane and/or the adhesive in the pellicle.

The pellicle membrane is produced preferably by membrane formation by using a solution of the polymer (1). The solvent is not particularly limited so long as it is capable of dissolving the polymer (1) of the present invention having fluorine atoms. It is preferred to select a solvent providing a high solubility to the polymer, and a fluorinated organic solvent is particularly preferred.

As specific examples of the fluorinated organic solvent, the following examples may be mentioned.

Polyfluoroaromatic compounds such as perfluorobenzene, pentafluorobenzene and 1,3-bis(trifluoromethyl)benzene. Polyfluorotrialkylamine compounds such as perfluorotributylamine and perfluorotripropylamine. Polyfluorocycloalkane compounds such as perfluorodecalin and perfluorocyclohexane. Polyfluorocyclic ether compounds such as perfluoro(2-butyltetrahydrofuran).

Polyfluoroalkanes such as perfluorooctane, perfluorodecane, 1,3-dichloro-1,1,2,2,3-pentafluoropropane, 2H,3H-perfluoropentane and 1H-perfluorohexane. Polyfluoroethers such as methyl perfluoroisopropyl ether, methyl perfluorobutyl ether, methyl (perfluorohexylmethyl) ether, methyl perfluorooctyl ether and ethyl perfluorobutyl ether.

As a method of producing a pellicle membrane from a solution of the polymer (1), a known method of forming a membrane from a solution may be employed, and a method of forming a thin membrane of the polymer on a substrate by means of a method such as roll coating, casting, dip coating, spin coating, water casting, die coating or Langmuir Blodgett, is preferred. In the case of a pellicle membrane, extremely strict membrane thickness control is required, and therefore it is more preferred to employ spin coating. As the substrate, preferred is a silicon wafer, quartz glass or the like having a smooth surface. The thickness of the pellicle membrane is usually preferably within a range of from 0.01 to 50 μm.

As the adhesive with which the pellicle membrane is bonded to the frame, it is preferred to use a polymer containing repeating units represented by the formula (1), particularly preferably a polymer containing repeating units represented by the formula (1) and having functional groups. Further, it is especially preferably a copolymer having repeating units of the formula (1) and units formed by polymerization of the monomer (3M-1) as essential components and having functional groups, a copolymer having repeating units of the formula (1) and units formed by polymerization of the monomer (3M-2) as essential components and having functional groups, or a copolymer having repeating units of the formula (1) and repeating units formed by polymerization of the monomer (3M-3) as essential components and having functional groups. Further, an adhesive polymer is not necessarily required to have high transparency, and accordingly the proportion of the repeating units represented by the formula (1) in the adhesive polymer may be small. For example, the proportion of the repeating units represented by the formula (1) to the entire repeating units in the polymer may be less than 1 mol %, and it is preferably at least 0.0001 mol % and less than 1 mol %.

Further, in a case where the polymer (1) of the present invention is used as an adhesive for a frame and a pellicle membrane for a pellicle, it is preferred to use an adhesive polymer in which functional groups effective to improve the adhesive properties are introduced. On the other hand, the polymer (1) of the present invention for a pellicle membrane is preferably a polymer having no functional group in view of light transmittance.

In a case where the adhesive polymer has functional groups, the functional groups are selected from functional groups which provide adhesive properties to the frame and the pellicle membrane, and they are preferably one or more types of groups selected from carboxyl groups, sulfonic acid groups, alkoxycarbonyl groups, acyloxy groups, alkenyl groups, hydrolyzable silyl groups, hydroxyl groups, maleimide groups, amino groups, cyano groups and isocyanate groups. Further, as such functional groups, particularly preferred are carboxyl groups, since favorable adhesive properties to a metal such as aluminum as a frame material can be obtained, such an effect is obtained at a relatively low temperature, and excellent storage stability will be obtained.

In a case where the adhesive polymer contains functional groups, the number of functional groups is preferably from 0.001 to 1 mmol per 1 g of the polymer. When the number of functional groups is at most 1 mmol, the properties to absorb a short wavelength light which the functional groups have are less likely to impair the durability of the adhesive.

The adhesive polymer having functional groups introduced may be prepared by a known method (e.g. JP-A-4-189880, JP-A-4-226177, JP-A-6-220232).

The method of introducing functional groups may, for example, be a method (1) wherein after the monomer (1M) is polymerized or after the monomer (1M) and the other monomer (3M) are polymerized, polymer terminal groups derived from e.g. a polymerization initiator or a chain transfer agent are utilized as functional groups, a method (2) of copolymerizing the monomer (1M), the other monomer (3M) and a polymer containing functional groups, or a method (3) wherein in the method (2), groups which may be converted into functional groups are introduced instead of the functional groups, and then such groups are converted into functional groups after the polymerization. Among them, it is preferred to employ the method (1) since the introduction operation is easily carried out.

As specific examples of a method of introducing carboxyl groups, a method (example of the method (3)) of copolymerizing a monomer having alkoxycarbonyl groups, and then converting the alkoxycarbonyl groups in the copolymer into carboxyl groups by a hydrolysis reaction, or a method (example of the method (1)) of forming a polymer having alkoxycarbonyl groups as terminal groups and hydrolyzing it, may be mentioned.

Further, as a method other than the above, a method of subjecting a polymer to a high temperature treatment so that the side chains or the terminals of the polymer are oxidatively destructed, to introduce carboxyl groups into the polymer, may, for example, be employed.

Further, as the adhesive, a polymer other than the polymer having repeating units represented by the formula (1) may be used. Such a polymer is not particularly limited, and compounds as disclosed in JP-A-2001-330943 or WO2001/37044 may be mentioned. Specifically, a polymer having no saturated alicyclic structure in its main chain, such as a propylene/vinylidene fluoride/tetrafluoroethylene copolymer or a vinylidene fluoride/hexafluoropropylene copolymer, or a copolymer containing vinylidene fluoride as the main component may, for example, be mentioned. It is preferred to introduce functional groups into such a polymer also by a method such as the method (1).

Further, in the present invention, e.g. a coupling agent of silane type, epoxy type, titanium type or aluminum type may be used together with the adhesive polymer, for the purpose of improving the adhesive property of the adhesive polymer.

Further, in a case where an adhesive polymer containing functional groups is used, the frame may be coated with the polymer thinly, and the surface thereof is coated with the fluoropolymer of the present invention containing no functional group, for bonding, whereby the pellicle frame can be strongly bonded.

The polymer containing repeating units represented by the formula (1) of the present invention is a novel polymer. The polymer may be used for applications other than a pellicle. In a case where the polymer is a copolymer, when the polymer is used for an application other than a pellicle, the proportion of repeating units other than the repeating units represented by the formula (1) is preferably at least 0.01 mass % and less than 100 mass %.

For example, the novel polymer of the present invention may have a low dielectric constant, and thus it may be utilized also as a protective film of a semiconductor element. Further, the polymer may have a low coefficient of water absorption, and thus it can insulate a semiconductor element from moisture. Namely, the polymer of the present invention may be utilized as an interlayer insulation film (for example, for a semiconductor element, for a liquid crystal display panel or for a multilayer wiring board), a buffer coating film, a passivation layer, an α-ray shielding film, an element sealing medium, an adhesive for various semiconductors (for example, for LOC or for die bonding), an interlayer insulation film for high-density mounting board, a moistureproof film for high frequency element (for example, a RF circuit element, a GaAs element or an InP element) or a protective film.

Further, the polymer of the present invention may be used as a film by itself, or as a film obtained by lamination with a resin such as a polyimide. The film may be utilized also as a film for a circuit board or for a film condenser.

EXAMPLES

Now, the present invention will be explained in further detail with reference to Examples. However, the present invention is by no means restricted to such specific Examples.

In GPC method, $M_w$ represents the weight average molecular weight and $M_n$ represents the number average molecular weight. Further, in Examples, gel permeation chromatography is represented as GPC method. A measuring means for the GPC method was in accordance with the method as disclosed in JP-A-2000-74892. Specifically, a mixed liquid of $CF_2ClCF_2CFHCl$ and $(CF_3)_2CHOH$ (volume ratio 99:1) was used as the mobile phase, and two columns of PLgel 5 μm MIXED-C (inner diameter 7.5 mm, length 30 cm) manufactured by Polymer Laboratories Ltd. were connected in series to obtain a column for analysis. As standard samples for molecular weight measurement, 10 kinds of polymethyl methacrylates having molecular weights of from 1,000 to 2,000,000 and having a molecular weight distribution ($M_w/M_n$) of less than 1.17 (manufactured by Polymer Laboratories Ltd.) were used to prepare an analytical curve. The molecular weight was obtained as a molecular weight calculated as polymethyl methacrylate, at a mobile phase flow rate of 1.0 ml/min, at a column temperature of 37° C., using an evaporative light scattering detector as a detector.

Example 1

Example of Production of Monomer (1M)

Example 1-1

Esterification Reaction

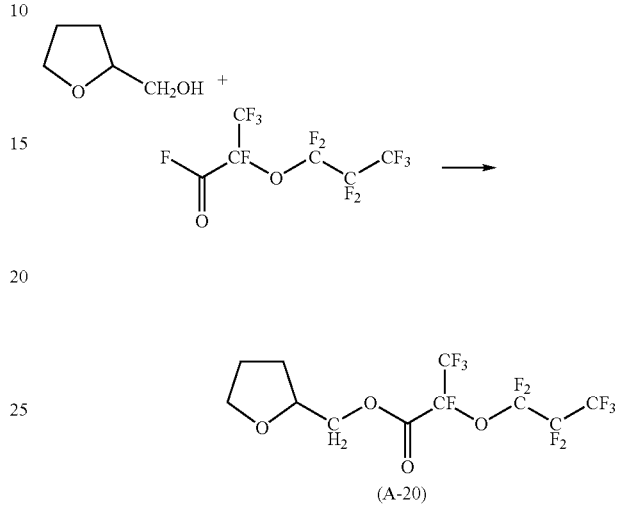

2-Tetrahydrofurfuryl alcohol (20 g) and $(CH_3CH_2)_3N$ (21.8 g) were put in a flask and stirred under cooling with ice. While keeping the temperature in the flask to at most 10° C., $FCOCF(CF_3)OCF_2CF_2CF_3$ (71.5 g) was dropwise added over a period of 1 hour. After completion of the dropwise addition, stirring was further carried out at 25° C. for 2 hours. Then, while keeping the temperature in the flask to at most 15° C., water (50 mL) was added to obtain a reaction liquid which was separated into two layers.

The reaction liquid was separated, and the lower layer was washed with water (50 mL) twice and dried over magnesium sulfate, followed by filtration to obtain a crude liquid. By distillation under reduced pressure, an aimed ester compound (66.3 g) was obtained as a fraction of 88 to 89° C./2.7 kPa (absolute pressure). The GC purity was 98%. Formation of compound (A-20) was confirmed by NMR analysis.

$^1$H-NMR (300.4 MHz, $CDCl_3$, TMS) δ (ppm): 1.60 to 1.73 (m,1H), 1.86 to 2.10 (m, 3H), 3.76 to 3.91 (m, 2H), 4.14 to 4.22 (m, 1H), 4.28 to 4.47 (m, 2H).

$^{19}$F-NMR (282.7 MHz, $CDCl_3$, $CFCl_3$) δ (ppm): −79.9 (1F), −81.3 (3F), −82.1 (3F), −86.4 (1F), −129.5 (2F), −131.5 (1F).

Example 1-2

Fluorination Reaction

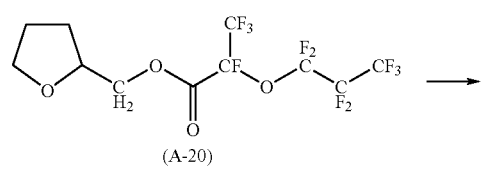

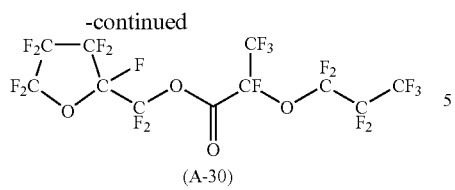

(A-30)

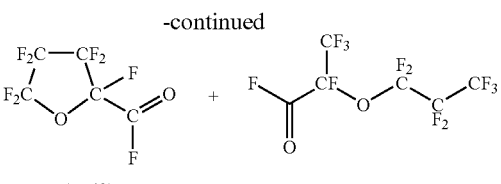

(A-40)

Into a 500 mL autoclave made of nickel, 1,1,2-trichloro-1,2,2-trifluoroethane (hereinafter referred to simply as R-113) (313 g) was added and stirred, and kept at 25° C. At the autoclave gas outlet, a condenser kept at 20° C., a NaF pellet packed bed and a condenser kept at −10° C. were disposed in series. A liquid return line which returns the condensed liquid from the condenser kept at −10° C. was disposed to the autoclave. A nitrogen gas was blown for 1.0 hour, and then a fluorine gas diluted to 20% with a nitrogen gas was blown at a flow rate of 8.08 L/h for 1 hour. Then, while blowing the fluorine gas at the same flow rate, a solution having compound (A-20) (5.01 g) obtained by esterification dissolved in R-113 (100 g) was injected over a period of 4.7 hours.

Further, while blowing the fluorine gas at the same flow rate, 9 mL of an R-113 solution having a benzene concentration of 0.01 g/mL was injected while increasing the temperature from 25° C. to 40° C., the benzene inlet of the autoclave was closed, and further, the outlet valve of the autoclave was closed, and when the pressure became 0.20 MPa, the fluorine gas inlet valve of the autoclave was closed, and stirring was continued for 0.4 hour. Then, the pressure was returned to the atmospheric pressure, and while keeping the temperature in the reactor at 40° C., 6 mL of the above benzene solution was injected, the benzene inlet of the autoclave was closed, and further, the outlet valve of the autoclave was closed, and when the pressure became 0.20 MPa, the fluorine gas inlet valve of the autoclave was closed, and stirring was continued for 0.4 hour. Further, the same operation was repeated three times. The total amount of benzene injected was 0.33 g, and the total amount of R-113 injected was 33 mL. Further, a nitrogen gas was blown for 1.0 hour. As a result of quantitative analysis of the aimed product by $^{19}$F-NMR, formation of compound (A-30) was confirmed, and the yield was 64%.

$^{19}$F-NMR (376.0 MHz, CDCl$_3$, CFCl$_3$) δ (ppm): −80.3 (1F), −81.9 (3F), −82.1 (3F), −83.5 to −84.8 (2F), −85.5 to −88.0 (3F), −126.5 (1F), −127.4 (1F), −128.1 (1F), −130.2 (2F), −130.4 (1F), −132.2 (1F), −135.8 (1F).

Example 1-3

Perfluoroester Pyrolysis Reaction

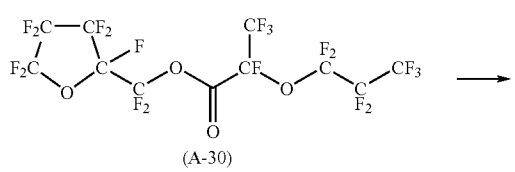

(A-30)

The compound (A-30) (2.1 g) obtained by fluorination was charged into a flask together with a NaF powder (0.02 g) and heated in an oil bath of 140° C. for 10 hours with vigorously stirring. A reflux condenser the temperature of which was adjusted to −10° C. was disposed at the upper portion of the flask. After cooling, a liquid sample (2.0 g) was recovered, which was precisely distilled to recover compound (A-40) (0.8 g). The structure of the compound (A-40) was confirmed by $^{19}$F-NMR.

$^{19}$F-NMR (376.0 MHz, CDCl$_3$, CFCl$_3$) δ (ppm): 26.6 to 26.3 (1F), −82.6 to −83.9 (2F), −117.9 to −118.3 (1F), −125.7 to −127.0 (2F), −128.9 to −129.9 (1F), −134.4 to −135.3 (1F).

Example 1-4

2,3,4,4,5,5-Hexafluoro-2,3-dihydrofuran Preparation Reaction

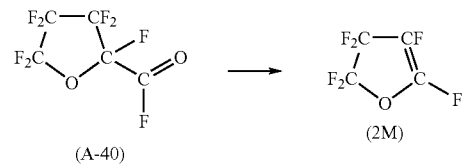

Soda glass beads (800 ml, trademark: Gakunan #150) were packed in a tubular reaction tube having an inner diameter of 5.2 cm and heated to 390° C. A nitrogen gas was flowed at a flow rate of 2.7 mol/h from the lower portion of the reactor to obtain a fluidized bed state, and the compound (A-40) obtained by the method of Example 1-3 was made to accompany the nitrogen gas and flow at 91 g/h (0.37 mol/h), to carry out a reaction. A reaction crude gas from the reactor outlet was recovered by a dry ice cooling trap and a liquid nitrogen cooling trap connected thereto. After reaction of 662 g (2.7 mol) of the material, a nitrogen gas alone was supplied for 1 hour to collect the entire reaction component gas remaining in the reactor. After completion of the reaction, the nitrogen gas trap was gradually heated to the dry ice cooling temperature, and the entire components which vaporize at this temperature were purged and then recovered as a collected gas. The crude products recovered by the dry ice cooling trap and the liquid nitrogen cooling trap were put together and 450 g of a crude liquid was recovered in total. As a result of analysis of the recovered liquid by GC, 10 mol % of the material, 70% of compound (2M) and 10% of an isomer represented by the following formula were contained.

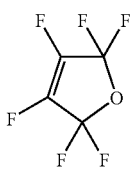

The recovered crude liquid was purified by distillation under elevated pressure (0.5 MPa) to isolate compound (2M), which was confirmed to have the following structure by $^{19}$F-NMR and GC-Mass spectral (EI detection) analysis:

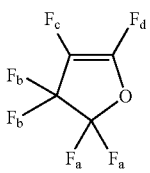

$^{19}$F-NMR (282.7 MHz, CDCl$_3$, CFCl$_3$) δ ppm: (−92.60 ppm, bs, 2F, Fa), (−113.95 ppm, dd, 2F, Jb-c=11 Hz, Jb-d=11 Hz, Fb), (−202.03 ppm, dt, 1F, Jc-d=20 Hz, Jc-b=11 Hz, Fc), (−107.90 ppm, dt, 1F, Jd-c=20 Hz, Jd-b=11 Hz, Fd).

Mass (EI method) m/z: 178(M$^+$), 159, 131, 128, 112, 109, 100, 93, 81, 69, 62, 50, 47 (calculated Exact mass of C$_4$F$_6$O: 177.99).

Example 2

Example of Production of Polymer B

Perfluoro(2-butyltetrahydrofuran) (20 g) and perfluoro(di(t-butyl)peroxide) (40 mg) as a polymerization initiator were put in an autoclave made of stainless steel and having an internal capacity of 100 ml, and the interior of the system was flushed with a nitrogen gas. Then, the autoclave was cooled to −78° C. in a dry ice/ethanol bath, and the compound (2M) (12.0 g) obtained in Example 1-4 was charged. Then, the interior of the system was pressurized to 0.5 MPa with a nitrogen gas, and polymerization was carried out at 100° C. for 36 hours. As a result, a polymer (hereinafter referred to as polymer B) (0.6 g) was obtained. As a result of $^{19}$F-NMR measurement of the polymer B, a peak attributable to fluorine atoms bonded to carbon atoms constituting the unsaturated bond completely disappeared, and it was confirmed that the furan ring structure was maintained.

The polymer B had M$_w$ of 1,350 by means of GPC method. The polymer B was a tough and transparent vitreous polymer. Further, as a result of measurement of T$_g$ by differential scanning calorimetric analysis (DSC method), it was 70° C.

Example 3

Example of Production of Polymer C and Adhesive D

Perfluoro(2-butyltetrahydrofuran) (20 g) and 15.4 mg of ((CH$_3$)$_2$CHOCOO)$_2$ as a polymerization initiator were put in an autoclave made of stainless steel and having an internal capacity of 100 mL, and the interior of the system was flushed with a nitrogen gas. Then, the autoclave was cooled to −78° C. in a dry ice/ethanol bath, and 2,2,3,3,4,5-hexafluoro-2,3-dihydrofuran (5.0 g) obtained in Example 1-4 and vinylidene fluoride (0.54 g) were charged. Then, the interior of the system was pressurized to 0.2 MPa with a nitrogen gas, and polymerization was carried out at 40° C. for 24 hours and further at 50° C. for 20 hours. As a result, a polymer (hereinafter referred to as polymer C) (2.5 g) was obtained. As a result of $^{19}$F-NMR measurement of the polymer C, the proportion of polymer units of the compound (2M) to the entire polymer units in the polymer C was 46 mol %, and the proportion of polymer units of vinylidene fluoride was 54 mol %. Further, in $^{19}$F-NMR spectrum of the polymer C, a peak attributable to fluorine atoms bonded to carbon atoms constituting the unsaturated bond completely disappeared, and it was confirmed that the furan ring structure was maintained.

The polymer C had M$_w$ of 75,000 by GPC method. Further, the polymer C was a tough and transparent vitreous polymer at room temperature. By measurement by means of thermogravimetric analysis in nitrogen, the 10% weight reduction temperature of this polymer was 443° C. Further, T$_g$ measured by DSC method was 80° C.

Then, the polymer C was charged in a hot air oven and treated while introducing oxygen at 300° C. for 2 hours. Then, the obtained polymer was immersed in pure water and treated at 100° C. for 24 hours, and the polymer was recovered and dried in vacuum at 100° C. for 24 hours. The IR spectrum of the obtained polymer (hereinafter referred to as polymer D) was measured, and a peak corresponding to carboxylic acid was confirmed. Hereinafter, this polymer will be referred to as adhesive D.

Example 4

Example of Production of Polymer E

Perfluoro(2-butyltetrahydrofuran) (5 g) and CF$_2$=CHCF(CF$_3$)CF$_2$OCF=CF$_2$ (hereinafter referred to simply as 5M monomer) (8.7 g) and perfluoro(di(t-butyl)peroxide) (60 mg) as a polymerization initiator were put in an autoclave (made of stainless steel, internal capacity 100 mL), the interior of the system was flushed with a nitrogen gas, and the autoclave was cooled to −78° C. in a dry ice/ethanol bath. The compound (2M) (6.5 g) obtained in Example 1-4 was charged in the autoclave. Then, the interior of the system was pressurized to 0.2 MPa with a nitrogen gas, and polymerization was carried out at 95° C. for 20 hours and further at 100° C. for 48 hours. As a result, a polymer (hereinafter referred to as polymer E) (6.3 g) was obtained. As a result of $^{19}$F-NMR measurement of the polymer E, the proportion of polymer units of the compound (2M) to the entire polymer units in the polymer E was 25 mol %, and the proportion of polymer units of the 5M monomer was 75 mol %. Further, in $^{19}$F-NMR spectrum of the polymer E, a peak attributable to fluorine atoms bonded to carbon atoms constituting the unsaturated bond completely disappeared, and it was confirmed that the furan ring structure was maintained.

The polymer E had M$_w$ of 22,000 by GPC method. Further, the polymer E was a tough and transparent vitreous polymer at room temperature. Further, as a result of measurement by DSC method, T$_g$ was 90° C.

Example 5 (Comparative Example)

Example of Production of Polymer F and Adhesive F 20 g of 1,1,2,4,4,5,5-heptafluoro-3-oxa-1,6-heptadiene and 40 g of 1H-perfluorohexane were put in an autoclave made of pressure resistant glass and having an internal capacity of 200 ml. 20 mg of bis(heptafluorobutyryl) peroxide as a polymerization initiator was added, and the interior of the system was flushed with nitrogen, and then polymerization was carried out at 40° C. for 10 hours. As a result, 15 g of a fluoropolymer having an alicyclic structure in its main chain (hereinafter referred to as polymer F) was obtained.

The intrinsic viscosity [η] of the polymer F was 0.96 dl/g in 1,3-bis(trifluoromethyl)benzene at 30° C. The polymer F had a glass transition temperature at 90° C., it was a tough and transparent vitreous polymer at room temperature, and it had a low refractive index of 1.36. On the other hand, the polymer F obtained in the same method as mentioned above was subjected to heat treatment in the air at 320° C. for 3 hours and then immersed in water and modified. By IR spectrum measurement of the modified polymer F, a peak attributable to a carboxyl group was confirmed, and the amount was 0.004 mmol/g. The modified polymer F will be hereinafter referred to as adhesive F.

Example 6

Preparation and Evaluation of Pellicle

Example 6-1

Example of Preparation of Membrane Employing Polymer E

The polymer E (2 g) prepared in Example 4 and perfluorotributylamine (18 g) were put in a glass flask and stirred with heating at 40° C. for 24 hours. As a result, a colorless transparent uniform solution without turbidity was obtained. The solution was coated on a polished quartz substrate by spin coating. The condition of spin coating was 10 seconds at a spinning speed of 500 rpm and then 20 seconds at 700 rpm. Further, heat treatment was carried out at 80° C. for 1 hour and further at 180° C. for 1 hour for drying, to form a uniform transparent membrane of the polymer E on the quartz substrate.

Example 6-2

Example of Preparation of Pellicle Employing Polymer E for Adhesive and for Pellicle Membrane The adhesive D (2 g) obtained in Example 3 and 1,3-bis(trifluoromethyl)benzene (38 g) were treated in the same manner as in Example 6-1 to obtain a uniform solution as adhesive E. The adhesive E was coated on the side of an aluminum frame on which a pellicle membrane was to be bonded, followed by drying at room temperature for 2 hours. Then the aluminum frame was put on a hot plate at 120° C. so that the adhesive surface turned up, followed by heating for 10 minutes, and the quartz substrate having the membrane of the polymer E formed thereon, obtained in Example 6-1, was overlaid and press-bonded on the aluminum frame so that the membrane surface of the quartz substrate was in contact with the adhesive surface of the frame. The assembly was further held at 120° C. for 10 minutes to complete bonding. Then, the thin membrane of the polymer E together with the aluminum frame was peeled from the quartz substrate. As a result, a pellicle having a uniform self-supporting membrane of about 1 μm in thickness made of the polymer E, bonded to the aluminum frame, by means of the adhesive E, was obtained. The membrane made of the polymer E had a transmittance of a light having a wavelength of 157 nm of at least 40%.

Example 6-3 (Comparative Example)

Example of Preparation of Pellicle Employing Polymer F for Adhesive and for Pellicle Membrane The polymer F (7 g) obtained in Example 5 and 1,3-bis(trifluoromethyl)benzene (93 g) are treated in the same manner as in Example 6-1 to obtain a uniform solution as adhesive F. The adhesive F is coated on an aluminum frame in the same method as in Example 6-2.

On the other hand, using the polymer F obtained in Example 5, in the same manner as in Example 6-1, a uniform transparent membrane of the polymer F was formed on a quartz substrate.

Then, in the same method as in Example 6-2, the aluminum frame is press-bonded and bonded to the membrane surface of the polymer F formed on the surface of the quartz substrate, followed by peel-off. As a result, a pellicle having a uniform self-supporting membrane of about 1 μm in thickness made of the polymer F, bonded to the aluminum frame by means of the adhesive F, is obtained. The membrane made of the polymer F has a transmittance of a light having a wavelength of 157 nm of at least 50%.

Example 6-4 (Example, Comparative Example)

Example of Evaluation of Durability of Pellicle

Each of the pellicle employing the polymer E obtained in Example 6-2 and the pellicle employing the polymer F obtained in Example 6-2 was subjected to an irradiation test by means of a $F_2$ excimer laser light having a wavelength of 157 nm, with an intensity of 0.05 mJ/pulse at a cycle of 200 Hz. As a result, in the pellicle employing the polymer E, the membrane showed excellent durability without no substantially decrease in transmittance with at least 600,000 pulses. Further, the pellicle membrane is strongly bonded to the frame by means of the adhesive, and favorable durability is confirmed.

On the other hand, in the pellicle employing the polymer F, the transmittance of the membrane decreased at a level of 40,000 pulses, and a decrease in durability was confirmed. Further, peeling of the pellicle membrane from the frame was confirmed, and the adhesive showed poor durability.

Example 7

Example of Production of Polymer A

Perfluoro(3-butenyl vinyl ether) (15 g), ion exchanged water (150 g) and a polymerization initiator (((CH$_3$)$_2$CHOCOO)$_2$, 90 mg) were put in an autoclave made of pressure resistant glass and having an internal capacity of 200 ml. The interior of the system was flushed with nitrogen three times, and then compound (2M) (15 g) was introduced, and the interior of the system was pressurized to 0.4 MPa with nitrogen, whereupon suspension polymerization was carried out at 40° C. for 22 hours. As a result, polymer A (16 g) was obtained. The intrinsic viscosity [η] of the polymer A was 0.40 in perfluoro(2-butyltetrahydrofuran) at 30° C. The polymer A had a glass transition point ($T_g$) of 128° C., and it was a tough and transparent vitreous polymer at room temperature. Further, the 10% thermal decomposition temperature was 460° C., and the refractive index was 1.33. In the $^{19}$F-NMR spectrum of the polymer A, a peak attributable to fluorine atoms bonded to carbon atoms constituting the unsaturated bond completely disappeared, and it was confirmed that the furan ring structure was maintained.

INDUSTRIAL APPLICABILITY

According to the present invention, a novel pellicle employing a specific polymer containing fluorine atoms as a pellicle membrane and/or an adhesive for a pellicle membrane is provided. Such a pellicle is an excellent pellicle from the viewpoint that it can be used for short wavelength photolithography. Further, a pellicle membrane having favorable transparency and excellent durability against light is provided. Further, an adhesive for a pellicle membrane having excellent adhesive property and durability is provided. According to the above present invention, an exposure method with which a semiconductor device can be produced with high yield in process of photolithography in production of a semiconductor device is provided.

The entire disclosure of Japanese Patent Application No. 2002-240759 filed on Aug. 21, 2002 including specification, claims and summary is incorporated herein by reference in its entirety.

What is claimed is:

1. 2,2,3,3,4,5-hexafluoro-2,3-dihydrofuran.

2. A polymer comprising polymer units represented by the following formula (2):

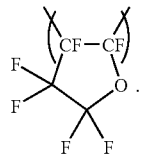

(2)

3. A polymer comprising:
   polymer units represented by the following formula (2), and
   one or more types of polymer units of other polymerizable monomers, wherein the polymer has a molecular weight of from 500 to 1,000,000, and the proportion of the polymer units represented by the formula (2) in the polymer is at least 0.01 mass % and less than 100 mass %:

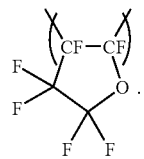

(2)

4. A method for producing a polymer comprising polymer units represented by the following formula (2), comprising:
   homopolymerizing 2,2,3,3,4,5-hexafluoro-2,3-dihydrofuran, or
   copolymerizing 2,2,3,3,4,5-hexafluoro-2,3-dihydrofuran with one or more types of other polymerizable monomers:

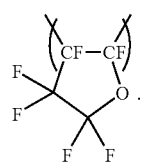

(2)

5. The polymer according to claim 2, wherein the polymer has a molecular weight of from 500 to 1,000,000.

6. The method according to claim 4, wherein the method comprises homopolymerizing 2,2,3,3,4,5-hexafluoro-2,3-dihydrofuran.

7. The method according to claim 4, wherein the method comprises copolymerizing 2,2,3,3,4,5-hexafluoro-2,3-dihydrofuran with one or more types of other polymerizable monomers.

* * * * *